United States Patent [19]

Bünger,

[11] 4,092,481

[45] May 30, 1978

[54] PROCESS FOR THE RECOVERY OF DIMETHYL TEREPHTHALATE AND OF INTERMEDIATES FROM THE DIMETHYL TEREPHTHALATE MANUFACTURE

[75] Inventor: Heinrich Bünger, Siegburg-Kaldauen, Germany

[73] Assignee: Dynamit Nobel Aktiengesellschaft, Germany

[21] Appl. No.: 585,760

[22] Filed: Jun. 10, 1975

[30] Foreign Application Priority Data

Jun. 10, 1974 Germany .............................. 2427875

[51] Int. Cl.$^2$ .............................................. C07C 69/82
[52] U.S. Cl. ......................................... 560/77; 560/78
[58] Field of Search ....................... 260/475 R, 475 B; 560/77, 78

[56] References Cited

U.S. PATENT DOCUMENTS 3,277,153  10/1966  Pieroh .................................. 260/475

FOREIGN PATENT DOCUMENTS 2,244,662   4/1974   Germany .......................... 260/475 R
2,327,773  12/1974   Germany .............................. 260/475
73/96539   12/1973   Japan .................................... 260/475

Primary Examiner—Jane S. Myers
Attorney, Agent, or Firm—Craig & Antonelli

[57] ABSTRACT

A process for the production of dimethyl terephthalate and intermediate products of the dimethyl terephthalate manufacture from the high-boiling by-products obtained during the air oxidation of p-xylene and methyl p-toluate in the liquid phase, subsequent esterification of the thus-formed acids, and separation of the thus-produced esters, which comprises treating said high-boiling by-products with methanol at an elevated temperature and then separating the resultant product rich in dimethyl terephthalate by distillation with the addition of a carrier gas or a carrier vapor.

16 Claims, No Drawings

PROCESS FOR THE RECOVERY OF DIMETHYL TEREPHTHALATE AND OF INTERMEDIATES FROM THE DIMETHYL TEREPHTHALATE MANUFACTURE

This invention relates to a process for obtaining dimethyl terephthalate (abbreviated hereinafter by DMT) and of intermediate products of the DMT manufacture, e.g. methyl p-toluate (PTE) or the methyl ester of terephthalaldehyde acid i.e. 4-formyl-benzoic acid (TAE) by the improved exploitation of the high-boiling tarry residues produced in significant amounts in the conventional processes for the preparation of DMT by the combined air oxidation of p-xylene and methyl p-toluate, subsequent esterification of the thus-formed acids with methanol, and subsequent separation of the esterification products. Heretofore, these residues could be utilized commercially to only an unsatisfactory extent; frequently, they are combusted. The technical usefulness thereof is also impaired, inter alia, by their consistency, because these are products which, at room temperature, are tacky, smeary, and highly viscous, which can only be pumped at higher temperatures and thus must be conveyed in expensive, heated pipelines or in expensive, heatable transport containers, and must be stored in expensive, heatable tanks.

DMT is required as the raw material for synthetic fibers and films or sheets on a large technical scale. Intermediates of the DMT manufacture, e.g. PTE and TAE, are converted technically by means of oxidation and subsequent esterification with methanol, thus producing DMT. Therefore, the production of DMT and of intermediate products of the DMT manufacture from the aforementioned low-quality, high-boiling tarry residues is of great technical interest.

A method is known from German Pat. No. 1,142,858 for obtaining methyl esters of diphenylpolycarboxylic acid from such high-boiling tarry residues wherein it is necessary, to achieve the object of the invention, to reduce by secondary esterification any possibly existing, more or less high acid numbers of these low-volatile, tarry residues before the isolation of the diphenylpolycarboxylic acid esters to be obtained therefrom. For this secondary esterification, the patent teaches to use preferably methanol. In this procedure, DMT is formed as a by-product and is separated from the residue containing diphenylpolycarboxylic acid by distillation under reduced pressure, in accordance with the teaching of this patent.

To obtain DMT from the low-volatile, tarry residues, the teaching of the German Pat. No. 1,142,858 is not particularly advantageous. According to this patent, the esterification with methanol is conducted in an autoclave at 250° C.; a reaction period of several hours is required for this purpose. The reactors needed for this process are therefore very large. However, for economical reasons, a small reactor volume is desirable, especially in case of pressure reactors. Furthermore, the yield of DMT according to the method of this patent is minor; German Pat. No. 1,142,858 indicates for this mode of operation a yield of 19.5% DMT + dimethyl isophthalate, using a charge of residue having an acid number of 80 mg. KOH/g. DOS [German Unexamined Laid-Open Application] No. 2,244,662 indicates for the same mode of operation a yield of 14.8% DMT, using a batch of residue having an acid number of 16 mg. KOH/g. Apparently, the acid number is a measure for the monomethyl terephthalate (MMT) and terephthalic acid content in the high-boiling tarry residue.

According to DOS No. 2,244,662, a higher DMT yield is attained if the methanol treatment of the high-boiling tarry residue is conducted above 250° C., preferably at 270°– 350° C., rather than at 250° C. This procedure also has disadvantages; although higher yields of DMT (21%) and intermediates of the DMT manufacture (5%) are produced, a complete exploitation of the low-volatile tarry residue has not yet been achieved by far. Also, the mode of operation according to DOS No. 2,244,662 has the disadvantage that it is necessary to provide for several hours of residence time and correspondingly large pressure reactors. The necessity of having to operate at reaction temperatures above 250° C. is of particular disadvantage, since reaction temperatures of more than 250° C. can no longer be maintained with the use of many customary, economical heat transfer fluids without impairing such heat transfer fluid.

According to German Pat. No. 1,192,638, intermediate products of the DMT manufacture can be obtained by alkaline hydrolysis of the high-boiling tarry residues; subsequent filtration; oxidation of the filtrate with permanganate, hypochlorite, or air; acidification with mineral acids, and filtration. One disadvantage of this process is that the final product is not DMT; rather, intermediate products of the DMT manufacture are obtained exclusively which must be converted into DMT by additional process steps.

Therefore, it is one of the objects of this invention to develop a process for obtaining DMT and intermediates of the DMT production from the aforementioned high-boiling tarry residues with a high reaction velocity and with high yields of DMT and with a maximally high yield of intermediates of the DMT manufacture.

A further object of this invention resides in the development of a process for obtaining DMT and intermediates of the DMT manufacture from the above-mentioned high-boiling tarry residues with a high reaction velocity and with high yields of DMT and with low pressure and with a maximally high yield of intermediates of the DMT manufacture at reaction temperatures which do not rise above 250° C. Consequently, it is another object of this invention to convert the high viscous, smeary by-products into those which flow at high temperatures but are flaky or granulated at normal temperature, and which can subsequently be stored and transported in bags, i.e. which are solid, friable, and brittle at normal temperature.

Additional objects and advantages of the invention can be seen from the following description.

The above-described problems are solved surprisingly by combining, according to this invention, a methanol treatment of the high-boiling tarry residue with a subsequent distillation with the addition of a carrier gas or a carrier vapor.

Insofar as known, there is no literature describing the advantageous utilization of a distillation with the addition of a carrier subsequently to a methanol treatment of the above-mentioned high-boiling tarry residues. Although the fine purification of crude DMT by means of carrier vapor distillation has been described occasionally, the starting material and the problem involved are entirely different than in the process of the present invention.

In the fine purification of crude DMT, a starting substance consisting primarily of DMT is subjected to a carrier vapor distillation to increase its degree of purity;

it has heretofore been unknown to attain an increase in the yield by means of this mode of operation.

In contrast thereto, in the process of this invention, a tarry residue of a complicated composition, containing only a small amount of DMT, is treated with methanol and subsequently the treated residue subjected to a distillation with the addition of a carrier gas or carrier vapor.

This process achieves, in a completely surprising manner, an increase in the yield of DMT and of intermediates of the DMT manufacture, as compared to the methods known heretofore including a vacuum distillation without carrier addition and described in German Pat. No. 1,142,858 and in DOS No. 2,244,662. It is particularly surprising that this increase in yield is not obtained, for example, by a higher physical degree of efficiency of the distillation by means of carrier addition, for even in a distillation without the addition of a carrier, e.g. under vacuum, the distillation can readily be conducted so that the DMT content of the distillation residue, as in a thorough carrier distillation, amounts to less than 1% by weight. Yet, the distillate fraction of the distillation with the addition of a carrier contains more DMT and more intermediates of the DMT manufacture than the distillate fraction of the distillation effected without a carrier. It seems as if, by means of the distillation with carrier addition, undesired secondary reactions of a nature not known in detail are being suppressed.

Low temperatures during the distillation with carrier addition have a positive influence on the yield, but with decreasing temperatures, an increased throughput of carrier gas or carrier vapor is required. Therefore, generally a temperature of no less than 150° C. will be maintained during the distillation with carrier addition; however, a minimum temperature of 170° C is to be preferred. Particularly suitable is a temperature of at least 190° C. Thus, the distillation with carrier addition may be conducted in the range of 150° C. to 300° C. and most preferably in a range of 190° C. to 220° C.

The pressure during the distillation with carrier addition is of significance insofar as less carrier is necessary under low pressure; while a higher pressure is more favorable for the condensation of the distillate. Therefore, in general, the distillation with carrier addition will be effected under at most 10 atmospheres gauge, while a pressure of at most 5 atmospheres gauge is to be preferred. In general, the process will be carried out at above 1 torr (mm. Hg), but a pressure of above 45 torr is to be preferred; especially suitable is a pressure of 1–2 atmospheres absolute because no expensive pressure or vacuum apparatuses are necessary during this process.

The distillation with carrier addition can be conducted batchwise as well as continuously. A continuous mode of operation is to be preferred. In this connection, an apparatus is suitable wherein the transfer of the DMT vapor into the carrier is accelerated by trays or other suitable devices. It is advantageous to free the carrier, which contains DMT and DMT preliminary products, from entrained residue mists in a column to which is introduced a small amount of reflux.

The amount of carrier required depends on the respective temperature, the respective pressure, and the apparatus employed. This quantity must be selected so that it does not fall short of the amount required for distilling off the DMT. For this purpose, it is suitable to withdraw samples from the distillation sump during the distillation, to determine the DMT content of these samples by analysis, and to adjust the amount of carrier as well as the duration of the distillation correspondingly. Generally, from 30 to 500 parts carrier par 100 parts by weight of the tarry residue used as a starting material are employed; whereas the duration of the distillation may vary from 0.1 to 20 hours.

It is advantageous to condense from the distillate of the carrier distillation a part of the DMT in a first condensation stage at a temperature of around 140° C., in order to avoid in this way a solidifcation of the condensate on the cooling surfaces. Thereafter, the residual DMT can be condensed together with the more volatile DMT preliminary products in a second condensation stage, wherein the initial DMT products obtained according to this invention sufficiently lower the melting point of the second condensate to avoid a solidification on the surfaces of the cooler.

The DMT can be separated from the condensed distillate of the distillation with carrier addition in accordance with known methods. In this connection, suitable is a crystallization under cold conditions from a suitable solvent, with subsequent filtration. If methanol vapor is used for the carrier distillation, the admixture of an additional solvent can be omitted, because methanol is an excellent solvent for crystallizing DMT from a solution. For this reason, methanol vapor is especially advantageous for use as a carrier. However, other vapors or gases can also be employed as the carrier, e.g. steam or the nitrogen-enriched exhaust air from the combined air oxidation of p-xylene and methyl p-toluate.

The filtrate obtained during a crystallization and filtration still contains a minor amount of DMT, in accordance with the solubility of the latter at the temperature employed for the crystallizing step. Also, this filtrate contains intermediates of the DMT manufacture, for example PTE and TAE, which can likewise be converted into DMT by oxidation and subsequent esterification with methanol. Therefore, it is advantageous for purposes of commercial exploitation to recycle that proportion of the distillate from the distillation with carrier addition, remaining after the separation of the crystallized DMT and the solvent, into a process for the DMT manufacture by combined air oxidation of p-xylene and PTE and subsequent esterification of the thus-formed acids with methanol. The separation of the solvent, after the crystallized DMT has been filtered off, takes place advantageously by means of distillation.

In contrast to the teaching in DOS No. 2,244,662, it is not necessary in the process of this invention to conduct the methanol treatment of the high-boiling tarry residue at temperatures above 250° C. to obtain a high DMT yield. According to the method of this invention, though, higher yields of DMT and of intermediates from the DMT manufacture than in the conventional process are also achieved even if the methanol treatment of the high-boiling tarry residue is conducted at reaction temperatures of up to 350° C. However, up to maximally 265° C. reaction temperature, customary economical heat transfer fluids, such as "Marlotherm" can be utilized with a certain limitation. "Marlotherm" is a commercial product of Chemische Werke Huls, Germany and is described in German Pat. Nos. 1,085,877 and 1,186,443. For this reason, a maximum reaction temperature of 265° C. is to be preferred. Especially advantageous is a maximum reaction temperature of 250° C.

The minimum temperature for the methanol treatment should not be below 180° C., because otherwise the required reaction periods become too long. A reaction temperature of at least 200° C. is to be preferred. Especially advantageous is a reaction temperature of above 220° C. Accordingly reaaction temperatures in the range of from 180° C. to 300° C. may be employed, with the most preferred range being from 220° C. to 250°C.

For reasons of economy, the presence during the methanol treatment of the high-boiling tarry residue should not be too high. However, the required reaction times become longer under low pressures. In general, the process will be carried out at between 0 and 60 atmospheres gauge.

The advantageous duration of the methanol treatment of the high-boiling tarry residue is dependent on the reaction temperature and pressure selected for this purpose. This period is suitably determined by withdrawing samples from the reactor during the methanol treatment and following the increase in DMT concentration. In general reaction times of between 5 minutes and 5 hours are utilized. However, more advantageously, the reaction time is less than 3 hours.

After a possible previous removal of the heavy metal oxidation catalyst customarily contained in high-boiling tarry by-products, longer residence times can be advantageous, especially in case of reaction pressures of below 5 atmospheres gauge.

The amount of methanol to be utilized according to the process of this invention can be methanol treatment of the high-boiling tarry residue can be varied within a wide range; however, this quantity is to be sufficient for setting the necessary reaction pressure at the selected reaction temperature. It is furthermore advantageous to withdraw during this methanol treatment a slight stream of methanol vapor from the reactor and replacing same constantly by fresh methanol, thereby to remove any possibly formed water of reaction from the reactor. In general, the amount of methanol utilized based on the amount of the high-boiling tarry residue is from about 30 to about 500 parts of methanol per 100 parts of the high-boiling tarry residue, i.e. by-products.

The methanol treatment of the high-boiling tarry residue can be effected discontinuously as well as continuously. With larger throughputs, the continuous mode of operation is especially advantageous.

Shorter residence times can be attained by making the process, especially the partial step of the carrier distillation, continuous; such shorter residence times are of special advantage for obtaining high yields.

In accordance with the above description, temperatures of 180°-300° C. and pressures of 0-10 atmospheres gauge are suitable for the methanol treatment of the high-boiling tarry by-products, as well as for the subsequent carrier distillation. In this temperature and pressure range, the methanol treatment of the high-boiling tarry by-products and the subsequent carrier distillation can advantageously be accomplished in the same column, by conducting high-boiling tarry by-products and methanol vapor countercurrently through the column, the by-products flowing through the column from the top toward the bottom. In this combined mode of operation in the same column, pressures of between 0 and 1 atmospheres gauge and temperatures of between 200° and 300° C. are to be preferred, wherein temperatures of between 220° and 265° C. are advantageous and those between 220° and 250° C. are of special advantage.

The methanol treatment of the high-boiling tarry residue does not necessitate any catalyst; however, it is also possible to accomplish this step in the presence of the conventional esterification and interesterification catalyst. In this connection, it can be advantageous to remove these catalysts before the subsequent carrier distillation.

The high-boiling tarry residues utilized in accordance with this invention normally contain all heavy metals added as catalysts in the combined air oxidation of p-xylene and PTE. The process of this invention can be employed with advantage in case these heavy metals are still present in the residues exploited according to the invention. However, the present process can also be employed particularly advantageously after these heavy metals have been removed from these residues, for example by a suitable extraction method. When the heavy metals are present, the residence times to be used are shorter. However, by a previous removal of the heavy metals from the by-products, the valuable heavy metals are recovered.

The process of this invention can be accomplished with the use of such high-boiling tarry residues stemming from a process for the DMT manufacture by the combined air oxidation of p-xylene and PTE in the presence of a unitary catalyst, e.g. a cobalt compound. However, the process of this invention can also be achieved especially advantageously with the use of such high-boiling tarry residues stemming from an air oxidation procedure operating with a combined oxidation catalyst, e.g. with a mixture of cobalt compounds and manganese compounds or nickel compounds and manganese compounds or cobalt compounds, nickel compounds, and manganese compounds, wherein the advantageous applicability of the process according to this invention is, however, nowise limited to high-boiling by-products stemming from air oxidations which work with these specifically mentioned catalyst components.

It makes no difference for the process of this invention whether or not the high-boiling tarry residues to be exploited according to this invention contain, due to their manufacture, an appreciable content of monomethyl terephthalate and free terephthalic acid and thus have a higher acid number. It is likewise unimportant whether or not the residues to be used according to this invention contain, due to their manufacture, an appreciable concentration of DMT. The advantages attainable by the process of the present invention are apparent if these aforementioned compounds are not contained in appreciable quantities, but they also manifest themselves if these above-mentioned compounds are present, because in such a case the amounts of DMT equivalent thereto are additionally obtained. Generally the content of DMT is from 1.0 to 25.0% by weight of the tarry residue. Even from production streams wherein the DMT content is higher than the content of high-boiling tarry by-products, DMT and initial DMT products can be advantageously obtained according to the process of this invention, because the amount of DMT already present in the product stream and the amount of DMT and initial DMT products obtainable from the content of high-boiling tarry by-products are simultaneously obtained. However, the quantity of the carrier must be adapted to the amount of the DMT to be removed by entrainment.

The advantages which can be obtained by means of this invention consist especially in that the yields of DMT are higher than in the heretofore known processes for obtaining DMT from the high-boiling tarry residues of the DMT manufacture by the combined air oxidation of p-xylene and PTE, esterification of the thus-formed acids, and working up of the thus-produced esters. Additionally, intermediate products of the DMT manufacture are obtained according to the process of this invention. Furthermore, the process makes it possible to operate with shorter reaction times and at lower reaction temperatures than in the heretofore known processes, thereby avoiding large pressure reactor volumes and special heating devices. It is furthermore possible according to this invention to convert smeary, tacky residues into brittle, glassy residues with high breaking hardness. A specific embodiment of the process of this invention makes it possible to attain the disclosed advantages without the use of expensive pressure and vacuum devices.

The following examples serve to further explain the invention.

EXAMPLE 1

At 130°–165° C., under a pressure of 6 atmospheres gauge and in the presence of 10 p.p.m. of manganese and 100 p.p.m. of cobalt, p-xylene and methyl p-toluate in a weight ratio of 1:2 were subjected together to an air oxidation. Both heavy metals were utilized in the oxidation reaction in the form of 2-ethylhexanoates. The oxidation product consisted predominantly of p-toluic acid and monomethyl terephthalate; this product was esterified with methanol at an elevated temperature and consisted in this case predominantly of methyl p-toluate and dimethyl terephthalate. At this point, the dimethyl terephthalate and all substances having a lower boiling point than dimethyl terephthalate were distilled off under vacuum, and the high-boiling distillation residue was then treated for 8 hours under vacuum at 240° C. Following this procedure, 500 g. of the thus-obtained high-boiling tarry residue contained 0.3% by weight of cobalt and 0.03% by weight of manganese, as well as according to analysis by gas chromatography, 20 g. of dimethyl terephthalate, less than 2.5 g. of monomethyl terephthalate, less than 2.5 g. of methyl p-toluate, less than 2.5 g. of the methyl ester of terephthalaldehydric acid, and less than 2.5 g. of p-toluyl-p-toluate. The acid number was 13.8 mg. KOH/g.

In an autoclave equipped with a check valve at the top 400 g. of methanol was pumped continuously at 250° C. and under a pressure of 24 atmospheres gauge within 60 minutes through 500 g. of these high-boiling tarry by-products. Vapor-phase methanol was withdrawn continuously through the check valve, which opened at 24 atmospheres gauge and was condensed in a cooler after expansion to atmospheric pressure.

After the one-hour methanol treatment was completed, the autoclave was cooled to an internal temperature of 210° C. and expanded at 210° C. to atmospheric pressure with the aid of the check valve; the thus-vaporized methanol was likewise condensed. After expansion, 2000 g. of methanol vapor having a temperature of 210° C. was conducted within 4 hours at 210° C. and 1 atmosphere absolute through the content of the autoclave, and the vapors leaving the autoclave were condensed. The condensate was freed from methanol in a forced circulation evaporator at 140° C. and under a vacuum produced by a water-jet aspirator; subsequently, the distillate product was analyzed by gas chromatography. The product containing 142 g. of DMT, 15 g. of methyl p-toluate, and 5 g. of the methyl ester of terephthalaldehydic acid. According to analysis by gas chromatography, the residue of the carrier vapor distillation contained 3.0 g. of DMT.

EXAMPLE 2

The mode of operation of Example 1 was repeated with 500 g. of the same high-boiling residues as characterized in Example 1, the only difference being that the distillation with addition of methanol vapor as carrier was conducted at 250° C. In this case, the distillate contained 125 g. of DMT, 12 g. of methyl p-toluate, and 4 g. of the methyl ester of terephthalaldehydic acid.

EXAMPLE 3

(Comparative Example)

The mode of operation according to Example 1 was repeated with 500 g. of the same high-boiling tarry by-products characterized in Example 1, the only difference being that a distillation under vacuum without the addition of carrier vapor was conducted in place of a carrier vapor distillation. The vacuum distillation was conducted at 50 torr and with a temperature gradually raised from 170° C. to 280° C. within 4 hours. The distillate was condensed and analyzed by gas chromatography; it contained 70 g. of dimethyl terephthalate, 10 g. of methyl p-toluate, and 7 g. of the methyl ester of terephthalaldehydic acid. The distillation residue contained 3.5 g. of dimethyl terephthalte, as determined by gas chromatography.

EXAMPLE 4

(Comparative Example)

The mode of operation according to Example 3 was repeated with the only difference that the vacuum distillation was conducted at a constant temperature of 210° C. In this instance, only 45 g. of DMT was found in the distillate.

EXAMPLE 5

The mode of operation according to Example 1 was repeated, the only difference being that the high-boiling tarry residue was agitated, prior to the methanol treatment, for 25 minutes at 95° C. with the same quantity by weight of a 5% aqueous acetic acid solution; thereafter, the mixture was allowed to settle for 25 minutes, the aqueous phase was separated, and the organic phase was dried at 80° C. and under 100 torr. According to this process, 500 g. of the organic phase contained 23 g. of dimethyl terephthalate, less than 2.5 g. of monomethyl terephthalate, 0.01% by weight of cobalt, and less than 0.01% by weight of manganese.

An amount of 500 g. of this nearly cobalt- and manganese-free residue was treated under elevated temperatures with methanol, exactly as described in Example 1, and then worked up by methanol vapor distillation. The distillate of the carrier vapor distillation contained 145 g. of dimethyl terephthalate, 17 g. of methyl p-toluate, and 7 g. of the methyl ester of terephthalaldehydic acid.

EXAMPLE 6

The mode of operation of Example 1 was repeated, except that the oxidation product was esterified with methanol only to an incomplete extent. After the esterification and the subsequent removal of the dimethyl terephthalate and the low-boiling substances by distillation under vacuum, a residue was obtained having an acid number of 70 mg. KOH/g.; 500 g. of this residue contained 30 g. of dimethyl terephthalate and 95 g. of monomethyl terephthalate. This residue was treated under elevated temperatures with methanol, exactly as described in Example 1, and was worked up by methanol vapor distillation. The distillate of the carrier vapor distillation yielded 238 g. of dimethyl terephthalate, 23 g. of methyl p-toluate, and 7 g. of the methyl ester of terephthalaldehydic acid.

EXAMPLE 7

The mode of operation of Example 1 was repeated, but instead of methanol vapor, 1,500 g. of steam was conducted, after the expansion of the autoclave, at 210° C. and 1 atmosphere within 4 hours through the product. The vapors leaving the reactor were condensed in a cooled receiver with a reflux condenser attached thereto. The condensate was dried under vacuum at 50° C., weighted, and analyzed. From 500 g. of high-boiling tarry by-products, there were thus obtained 123 g. of DMT, 11 g. of PTE, and 4 g. of TAE.

EXAMPLE 8

Low-volatile tarry by-products were obtained as in Example 1 by the common oxidation of p-xylene and PTE with air in the presence of cobalt and manganese catalysts, esterification of the thus-produced acids with methanol, and distillative separation of the thus-formed esters. The low-volatile tarry by-products contained 4.0% by weight of DMT, less than 0.5% by weight of PTE, less than 0.5% by weight of TAE, and less than 0.5% by weight of monomethyl terephthalate. They were viscous at 20° C. and not brittle.

The by-products were heated to 250° C. and pumped under normal pressure to the fourth plate, as counted from the top, of a bubble cap column. The latter contained 12 plates (trays) in total. The column was insulated against heat losses.

The by-products flowed downwardly within the column and were collected in a residue receiver disposed underneath the column. The speed with which the by-products were added was adjusted so that the residence time of the tarry by-products in the column was 3 hours. Countercurrently to the low-volatile tarry by-products, 4 parts by weight of methanol vapor of 250° C. temperature were conducted per part by weight of by-product through the column. The methanol vapor, laden with DMT and initial DMT products then left the column overheat at a temperature of 220° C. The methanol vapor was then conducted through a first condenser maintained at 140° C., then through a second condenser maintained at 15° C. In the first condenser, a condensate was separated consisting of 60% by weight DMT. One fifth of this condensate was returned into the column as reflux. The remainder was combined with the condensate obtained in the second condenser. The combined condensates were freed of methanol in a rotary evaporator (forced circulation evaporator), weighed, and analyzed by gas chromatography. During a 10-hour operation, 100 kg. of residue was utilized in this column, yielding 29.7 kg. of DMT, 4.7 kg of PTE, 2.0 kg. of TAE, and 2.0 kg. of p-methoxymethylbenzoic acid methyl ester. At the same time, 61 kg. of a residue was obtained which was, at 20° C., of glassy brittleness and could readily be shattered into shards with a hammer; these shards could be transported in bags.

EXAMPLE 9

(Comparative Example)

The mode of operation of Example 8 was repeated with the modification that high-boiling tarry by-products and methanol vapor were conducted through the column countercurrently under a pressure of 24 atmospheres gauge. The methanol vapor left the column overhead through a check valve opening at 24 atmospheres gauge, and then flowed through the same condensers as in Example 7. Under these conditions, the reaction products were not separated, since the DMT did not distill overhead in sufficient amounts. For this reason, no product was obtained in the first condenser, which was kept at 140° C., and no reflux could be pumped to the column. In the second condenser, methanol and some water were primarily obtained, and additionally minor amounts of DMT and PTE.

The residue, after flowing through the column, was collected in the residue receiver and discharged through a valve. The product was tacky; 100 kg. contained merely 24.8 kg. of DMT, 3.0 kg. of PTE, 1.8 kg. of TAE, and 2.0 kg. of p-methoxymethylbenzoic acid methyl ester. The residue was separated by evaporating the methanol dissolved therein and subsequent distillation at 50 torr (mm. Hg) and with a temperature which was gradually raised from 170° C. to 280° C. Although the DMT content of the sump product was lowered to 0.6% by weight, the distillate contained merely 18.5 kg. of DMT per 100 kg. of residue.

EXAMPLE 10 p-Xylene and PTE were oxidized together with air in the presence of cobalt and manganese catalysts. The thus-obtained acids were esterified with methanol, and the thus-formed esters were separated by vacuum distillation into a distillate fraction containing predominantly DMT, PTE, AE, and benzoic acid methyl ester, and a sump fraction containing primarily low-volatile by-products and no more than 4.5% by weight of DMT. The distillate fraction was again distilled under vacuum, thus distilling off the components having a lower boiling point than DMT, and the DMT was obtained, together with all components having a higher boiling point than DMT, as the sump product. This sump product was recrystallized from methanol and separated by centrifuging into a crystallized product consisting predominantly of DMT and into the mother liquor. From the mother liquor, the methanol was distilled off under normal pressure, and a high-boiling "filtrate residue" was obtained. The latter contained 19.0% by weight of DMT, 22.0% by weight of PTE, 0.8% by weight of AE, and 12.0% by weight of high-boiling by-products. The "filtrate residue" was heated, analogously to the mode of operation in Example 8, to 250° C. and pumped to the plate which is the fourth from the top of the bubble tray column described in Example 8. Countercurrently, 4 parts by weight of methanol vapor having a temperature of 250° C. were conducted through the column per part by weight of filtrate residue. The methanol vapor, laden with DMT and initial (preliminary) DMT products was condensed, as described in Example 7, in two condensers, whereby a partial stream was returned into the column as reflux, and the residual condensate was combined, freed of methanol, weighed, and analyzed. From 100 kg. of filtrate residue, one obtained 21.0 kg. of DMT, 23.0 kg. of PTE, and 0.8 kg. AE.

EXAMPLE 11 p-Xylene and PTE were oxidized together with air in the presence of cobalt and manganese catalysts. The thus-obtained acids were esterified with methanol, and the thus-formed esters were separated by vacuum distillation into a head product consisting primarily of benzoic acid methyl ester, PTE, and AE, and into a distillation residue consisting according to analysis by gas chromatography of 85.0% by weight of DMT and 6.0% by weight of higher-boiling by-products. This distillation residue was continuously pumped at 250° C. temperature and under normal pressure to the fourth plate, counted from the top, of the bubble tray column described in Example 8. Per part by weight of this distillation residue, 16 parts by weight of methanol vapor having a temperature of 250° C. were conducted countercurrently through the column. The DMT-laden methanol vapor was then withdrawn overhead as in Example 8 and condensed. One-fifth of the condensate from the first condenser was returned to the column as reflux. The remainder was combined with the condensate obtained in the second condenser. The combined condensates were freed of methanol in a forced circulation evaporator, weighed, and analyzed. From 100 kg. of product employed, the yield was 87.6 kg. of DMT, although the product employed contained merely 85.0% by weight of DMT.

What is claimed is:

1. A process for the production of dimethyl terephthalate and intermediate products of the dimethyl terephthalate manufacture from the high-boiling by-products obtained during the combined air oxidation of p-xylene and methyl p-tolute in the liquid phase, subsequent esterification of the thus-formed acids, and separation of the thus-produced esters by distillation, characterized in that these by-products are first treated with methanol at temperatures between 180° C. and 350° C. and under pressures of between 0 and 60 atmospheres gauge in an amount sufficient for setting the necessary reaction pressure at the selected reaction temperature and are then separated by distillation with the addition of a carrier gas or a carrier vapor at temperatures of between 150° C. and 300° C. and under pressures of between 1 torr and 10 atmospheres gauge to thereby provide a high yield of dimethyl terephthalate and a high yield of the intermediate product of the dimethyl terephthalate manufacture.

2. A process according to claim 1, characterized in that methanol vapor is used as the carrier gas.

3. A process according to claim 1, characterized in that the treatment of the by-products with methanol at an elevated temperature and the distillation with the addition of a carrier are conducted continuously.

4. A process according to claim 1, characterized in that the methanol treatment and the subsequent distillation with the addition of a carrier is conducted continuously in the same column under pressures of between 1 and 11 atmospheres absolute and at temperatures of between 180° and 300° C.

5. A process for the production of dimethyl terephthalate and intermediate products of the dimethyl terephthalate manufacture from the high-boiling by-products obtained during the combined air oxidation of p-xylene and methyl p-toluate in the liquid phase, subsequent esterification of the thus-formed acids, and separation of the thus-produced esters by distillation, characterized in that these by-products are first treated with methanol at an elevated temperature in an amount sufficient for setting the necessary reaction pressure at the selected reaction temperature and are then separated by distillation with the addition of a carrier gas or carrier vapor to thereby provide a high yield of diimethyl terephthalate and a high yield of the intermediate product of the dimethyl terephthalate manufacture, the methanol treatment and the subsequent distillation with the addition of a carrier being conducted continuously in the same column under pressures of between 1 and 2 atmospheres absolute and at 220°–250° C.

6. A process according to claim 5, characterized in that the carrier gas is methanol vapor.

7. A process according to claim 1, characterized in that the process is conducted with products stemming from a process for the combined air oxidation of p-xylene and methyl p-toluate in the presence of a unitary oxidation catalyst.

8. A process according to claim 1, characterized in that the process is conducted with high-boiling by-products stemming from a process for the combined air oxidation of p-xylene and methyl p-toluate in the presence of a combined oxidation catalyst.

9. A process according to claim 8, characterized in that the process is conducted with high-boiling by-products stemming from a procedure for the common air oxidation of p-xylene and methyl p-toluate in the presence of a cobalt-manganese catalyst.

10. A process according to claim 1, characterized in that the process is conducted with high-boiling by-products produced from the combined air oxidation of p-xylene and methyl p-toluate in the presence of an oxidation catalyst and from which the oxidation catalyst has been removed.

11. A process according to claim 1, characterized in that the methanol used in the methanol treatment is from about 30 to about 500 parts per 100 parts of the high-boiling by-products.

12. A process according to claim 11, characterized in that the amount of carrier gas added is from about 30 to 500 parts by weight per hundred parts by weight of the tarry by-products.

13. A process according to claim 1, characterized in that the carrier gas is a gas which remains in the gaseous phase during said distillation and which does not react with the products treated with methanol at the distillation conditions.

14. A process according to claim 1, characterized in that the amount of carrier gas or vapor is in a sufficient amount to distill off dimethyl terephthalate.

15. A process according to claim 1, characterized in that the duration of the methanol treatment is from 5 minutes to 5 hours and the duration of the distillation in the presence of a carrier gas or carrier vapor is from 0.1 to 20 hours.

16. A process according to claim 1, further comprising effecting recovery of the dimethyl terephthalate from the distillate of the carrier distillation by initially condensing a part of the dimethyl terephthalate from the distillate in a first condensation stage at a temperature of about 140° C., then condensing the residual dimethyl terephthalate together with more volatile dimethyl terephthalate preliminary products in a second condensation stage and thereafter separating dimethyl terephthalate from the condensed distillate of the distillation with carrier addition by crystallization and subsequent filtration.

* * * * *